(12) United States Patent
Robert et al.

(10) Patent No.: US 11,396,027 B2
(45) Date of Patent: Jul. 26, 2022

(54) SPRAY ARM SPEED REGULATOR

(71) Applicant: STERIS INC., Temecula, CA (US)

(72) Inventors: Maxime Robert, L'Ancienne-Lorette (CA); Alain Chouinard, Quebec (CA)

(73) Assignee: STERIS INC., Temecula, CA (US)

(*) Notice: Subject to any disclaimer, the term of this patent is extended or adjusted under 35 U.S.C. 154(b) by 69 days.

(21) Appl. No.: 16/701,525

(22) Filed: Dec. 3, 2019

(65) Prior Publication Data
US 2021/0162431 A1 Jun. 3, 2021

(51) Int. Cl.
*B05B 3/04* (2006.01)
*B05B 3/06* (2006.01)

(52) U.S. Cl.
CPC ............ *B05B 3/0472* (2013.01); *B01L 13/00* (2019.08); *B05B 3/063* (2013.01)

(58) Field of Classification Search
CPC ....... B05B 3/0472; B05B 3/063; B05B 3/066; B05B 3/0481; B01L 13/00
USPC ..................................... 239/7, 230, 231, 233
See application file for complete search history.

(56) References Cited

U.S. PATENT DOCUMENTS

| | | | | |
|---|---|---|---|---|
| 270,664 A | * | 1/1883 | Henderson | B05B 3/08 239/231 |
| 1,022,643 A | * | 4/1912 | Schellenger | B05B 1/267 239/511 |
| 1,798,488 A | * | 3/1931 | Orr | B05B 17/06 239/227 |
| 2,016,743 A | | 10/1935 | Ghislain | |
| 2,314,702 A | | 3/1943 | Higgins | |
| 2,987,260 A | * | 6/1961 | Sasnett | A47L 15/23 239/231 |

(Continued)

FOREIGN PATENT DOCUMENTS

| | | |
|---|---|---|
| CN | 203724060 U | 7/2014 |
| KR | 10-0267927 B1 | 7/2000 |
| KR | 10-1933872 B1 | 12/2018 |

OTHER PUBLICATIONS

International Search Report issued in corresponding International Application No. PCT/US2020/060133 dated Apr. 20, 2021.

(Continued)

*Primary Examiner* — Steven J Ganey
*Assistant Examiner* — Kevin Edward Schwartz
(74) *Attorney, Agent, or Firm* — Kusner & Jaffe

(57) ABSTRACT

Rotational speed of a spray arm is regulated based on centrifugal force and a liquid jet to create a variable angle corner spray nozzle. The regulator includes a weight on a pivot and a fluid jet, the weight having a curved surface to produce a variable angle corner spray nozzle depending on the weight angle. Centrifugal force created during rotation pushes the weight outward, which increases as the spray arm rotation speed increases. The liquid jet is located out from a pivot point and tends to push the weight inward. The pushing force of the liquid jet is maximum when the weight is most inward and minimum when the weight is most outward. The regulator stabilizes the arm speed at a specific speed independent from center pivot friction and the spray arm nozzle's orientation tolerance. Speed stabilizes when centrifugal force on the weight is equal to the pushing force of the fluid jet.

18 Claims, 4 Drawing Sheets

(56) References Cited

U.S. PATENT DOCUMENTS

| | | | | |
|---|---|---|---|---|
| 3,005,593 A | * | 10/1961 | Smith | B05B 3/06 |
| | | | | 239/252 |
| 3,144,034 A | * | 8/1964 | Lyman | B05B 3/0486 |
| | | | | 239/265.17 |
| 3,496,949 A | * | 2/1970 | Mercer | A47L 15/23 |
| | | | | 134/179 |
| 3,915,182 A | * | 10/1975 | Payne | A47L 15/23 |
| | | | | 134/176 |
| 3,979,066 A | * | 9/1976 | Fortner | B05B 3/06 |
| | | | | 239/252 |
| 4,234,126 A | * | 11/1980 | Morgan | B05B 3/0472 |
| | | | | 239/230 |
| 5,673,714 A | | 10/1997 | Campagnolo et al. | |
| 7,841,104 B2 | | 11/2010 | Robert et al. | |
| 8,448,654 B2 | | 5/2013 | Turner et al. | |
| 9,211,051 B2 | * | 12/2015 | Billgren | A47L 15/23 |
| 9,295,368 B2 | | 3/2016 | Feddema | |
| 2010/0163644 A1 | | 7/2010 | Dieziger | |
| 2012/0175431 A1 | | 7/2012 | Althammer | |
| 2013/0043164 A1 | | 2/2013 | Hatten | |
| 2018/0035863 A1 | | 2/2018 | Liu et al. | |

OTHER PUBLICATIONS

Written Opinion issued in corresponding International Application No. PCT/US2020/060133 dated Apr. 20, 2021.

\* cited by examiner

SPRAY ARM SPEED REGULATOR

FIELD OF THE INVENTION

The invention pertains to a spraying arm for a cleaning machine for cleaning medical, pharmaceutical and/or laboratory utensils and, more particularly, regulating a rotational speed of a spraying arm.

BACKGROUND OF THE INVENTION

Cleaning machines, such as dishwashers or machines for cleaning and disinfecting medical, pharmaceutical, and/or laboratory utensils, include a spraying compartment into which a trolley for holding the objects to be cleaned can be introduced. One or more spraying arms spray a liquid, such as water or other cleaning liquid, through spray apertures at a high pressure in an upward and/or downward direction to flush and clean utensils in the spraying compartment.

Typically the spraying compartment has a non-circular form-factor, e.g., rectangular shape, while the spraying arm sprays in a circular pattern. A consequence of the circular pattern is that corner portions of the spraying compartment may not receive sufficient (or any) cleaning fluid and thus utensils placed in this portion of the spraying compartment may not be adequately cleaned. To address this problem, additional spray nozzles are placed at the end of the spray arm and angled to target the corner portions. For example, a nozzle at one end can be angled slightly upward and a nozzle at the other end can angled slightly downward. For low pressure/high flow systems, a simple jet may be arranged on a side of the spray arm near the tip. For high pressure systems, it is preferable to use an angle spray nozzle to minimize flow.

Due to the direction at which the liquid cleaner is sprayed, these corner spray nozzles create a force that causes rotation of the spraying arm. To provide effective cleaning, it is preferable that the cleaning liquid be sprayed at a high pressure and a specified speed. Such high pressure, however, tends to cause excessive rotational speed of the spraying arm which necessitates a means for regulating the rotational speed of the spraying arm.

Conventionally, the rotational speed of the spraying arm is set by selecting specific angles and pressures at which the corner spray nozzles emit the liquid cleaner. For example, a trial and error process may be performed where the tilt angle of the corner spray nozzle is adjusted until speed is within a desired range. This process, however, is time consuming and it can be difficult to achieve precise results, particularly with long spray arms that require lower rotational speeds. Further, due to manufacturing tolerances it can be difficult to achieve low-speed rotation using fixed/adjustable corner nozzles.

SUMMARY OF THE INVENTION

A device and method in accordance with the invention enable a rotational speed of a spray arm to be precisely regulated. A spray arm speed regulator in accordance with the invention uses centrifugal force and a liquid jet to create a variable angle corner spray nozzle that regulates spray arm rotation speed. The regulator includes a weight on a pivot with a water jet, the weight having a curved surface to produce a variable angle corner spray nozzle depending on the angle of the weight relative to the nozzle. Centrifugal force created during rotation pushes the weight outward, which increases as the spray arm rotation speed increases. The water jet is located out from a pivot point and tends to push the weight inward. The pushing force of the water jet is maximum when the weight is most inward and minimum when the weight is most outward. Speed stabilizes when centrifugal force on the weight is equal to the pushing force of the water jet. The regulator in accordance with the invention stabilizes the arm speed at a specific speed independent of center pivot friction and the spray arm nozzle's orientation tolerance.

According to one aspect of the invention, a device for a cleaning machine includes: an arm rotatable about an axis, the arm including a first arm portion and a second arm portion diametrically opposite the first arm portion; a first nozzle disposed on the first arm portion; a first deflector pivotably connected at the first arm portion and arranged to receive a stream of fluid emitted from the first nozzle; and wherein fluid emitted from the first nozzle strikes the first deflector and causes a force that tends to pivot the first deflector toward the first arm portion to rotate the arm, and rotation of the arm about the axis causes a force that tends to pivot the first deflector away from the first arm portion.

In one embodiment, the device includes a base, wherein the arm is rotatably connected to the base about the axis.

In one embodiment, a pivot point for the first deflector is located radially inward relative to the first nozzle.

In one embodiment, the first deflector includes a proximal surface having a curved portion, and the proximal surface is disposed adjacent to the first nozzle.

In one embodiment, the curved portion produces a fan spray pattern between 10 degrees and 90 degrees.

In one embodiment, a pushing force of fluid emitted from the first nozzle increases as the first deflector is pivoted toward the first arm portion.

In one embodiment, a pushing force of fluid emitted from the first nozzle decreases as the first deflector is pivoted away from the first arm portion.

In one embodiment, the first deflector includes a distal surface having a chamfer.

In one embodiment, fluid emitted by the first nozzle creates a force that rotates the arm about the axis, the force varying based on a distance of the first deflector relative to the first arm portion.

In one embodiment, the first nozzle is arranged at an outer end of the first arm portion.

In one embodiment, the device includes: a second nozzle disposed on the second arm portion; and a second deflector pivotably connected at the second arm portion and arranged to receive a stream of fluid emitted from the second nozzle.

According to another aspect of the invention, a method for regulating a speed of a spray arm about an axis is provided, wherein the spray arm includes at least one deflector pivotably attached to the spray arm and having a curved surface, and at least one nozzle arranged relative to the curved surface. The method includes: emitting fluid from the at least one nozzle to strike the curved surface and cause i) a first force that tends to pivot the at least one deflector toward the spray arm, and ii) a second force that tends to rotate the spray arm about the axis, wherein rotation of the spray arm about the axis causes a third force that tends to pivot the at least one deflector away from the spray arm, whereby a balance between the first force and the third force is achieved at a predefined rotational speed.

In one embodiment, the method includes selecting at least one of a weight of the at least one deflector or a pivot location of the at least one deflector to achieve the predefined speed.

In one embodiment, the method includes defining a shape of the curved surface to achieve the predefined speed.

In one embodiment, the third force is a centrifugal force.

In one embodiment, fluid striking the surface creates a fan-type spray pattern.

In one embodiment, the fan-type spray pattern is between 10 degrees and 90 degrees.

In one embodiment, the second force increases as the deflector pivots toward the spray arm.

In one embodiment, the second force decreases as the deflector pivots away from the spray arm.

To the accomplishment of the foregoing and related ends, the invention, then, comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein.

DETAILED DESCRIPTION OF PREFERRED EMBODIMENT

Figure 1:
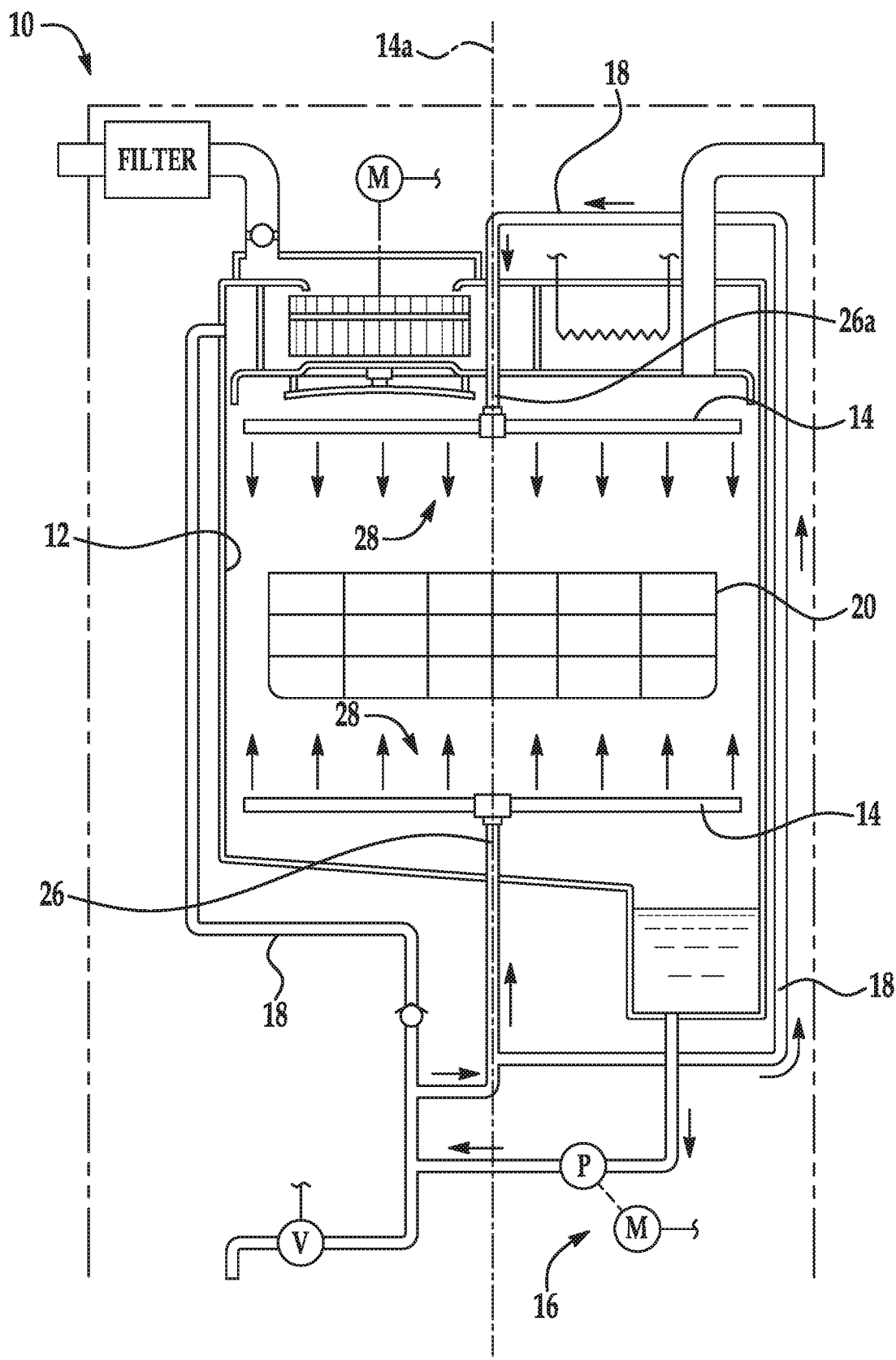
FIG. 1 is a side view of an exemplary cleaning machine to which principles in accordance with the present invention may be applied.

Embodiments of the present invention will now be described with reference to the drawings, wherein like reference numerals are used to refer to like elements throughout. It will be understood that the figures are not necessarily to scale. Further, the invention finds utility in cleaning machines that use a liquid to perform the cleaning operation and, therefore, the invention will be described chiefly in this context. However, principles of the invention may be applied to other types of devices and/or may use a fluid (e.g., compressed air, etc.) instead of a liquid as the primary medium.

Referring to FIG. 1, cleaning machines 10, such as dishwashers or machines for cleaning and disinfecting medical, pharmaceutical, and/or laboratory utensils, typically have a spraying compartment 12 for cleaning the utensils, the spraying compartment 12 including at least one rotating spraying arm 14. The spraying arm 14 rotates around a vertical axis 14a to supply a liquid medium to the utensils placed within the cleaning compartment 12, the liquid medium supplied under pressure via pump assembly 16 and associated flow channels 18. Removable bins 20 for holding utensils to be cleaned are arranged in the spraying compartment 12 and are sprayed with a cleaning liquid emitted from the spraying arm 14.

The spraying arm 14 is supported on a pedestal 26 mounted to a floor of the spraying compartment 12, where the spraying arm 14 sprays cleaning liquid up toward the utensils. Additionally, another spraying 14 arm may be suspended from an over-head support 26a and spray cleaning liquid down onto the utensils.

Each spraying arm 14 includes outlet nozzles 28 for producing jets of spraying liquid aimed in a predetermined jet direction, which typically is at an angle of more than 0 degrees and less than 90 degrees to the rotation direction of the spraying arm. The spraying arms 14 are driven around their rotational axis 14a by the force of the appropriately aimed jets of liquid medium emerging from the spraying arms 14. Additional details concerning the cleaning machine 10 can be found in U.S. Pat. No. 7,841,104, which is incorporated by reference in its entirety.

As will be appreciated, the cleaning machine 10 and arrangement of spraying arms 14 may take on many forms, and the embodiment referenced above is merely exemplary of a few ways in which a cleaning machine may be configured. For example, the cleaning machine may include a spraying arm mounted to a movable trolley. In yet other embodiments, instead of a spraying compartment 12 an open configuration may be implemented (e.g., without walls). Such "open" embodiment may be practical in an industrial setting where large objects are cleaned.

Conventionally, the rotational speed of the spraying arm 14 is set by selecting specific angles and pressures at which the corner spray nozzles emit the liquid. Due in part to manufacturing tolerances, this process does not produce consistent results. Moreover, the process is time consuming and, as the spray arm length increases, it can be difficult to achieve precise results.

In accordance with the present invention, a rotational speed of a spraying arm is regulated using a pivotably-mounted liquid-stream deflector having a curved surface with a fixed radius. As described in more detail below, depending on a pivot position of the deflector relative to a liquid nozzle, a liquid stream emitted from the nozzle is deflected at different angles relative to a direction of rotation of the spraying arm. Since the liquid stream angle can be varied relative to the rotation direction of the arm, a "push" force created by the stream (which rotates the arm) can be varied. In this regard, the curved surface is configured such that a pushing force created by liquid emitted from the nozzle and striking the curved surface increases as the deflector is pivoted in toward the arm. Conversely, the pushing force of liquid emitted from the nozzle and striking the curved surface decreases as the deflector is pivoted away from the arm. As discussed in more detail below, the liquid stream striking the deflector tends to pivot the deflector in toward the arm (creating maximum "push") and, as the arm rotates, centrifugal force tends to pivot the deflector away from the arm (decreasing the "push"). The two forces reach an equilibrium at a predetermined rotational speed.

For example, with the spraying arm initially in the stopped position, liquid is emitted from a nozzle located at an end of the spraying arm at a predetermined pressure. The liquid strikes the curved surface of the deflector with a first force, causing the deflector to pivot toward the spraying arm. At the same time, the emitted liquid is deflected at an angle relative to the rotation direction of the arm, thereby creating a second "pushing" force. While the deflector is pivoted in toward the arm the pushing force is at a maximum, causing the arm to accelerate. As the arm increases in speed, centrifugal force causes the deflector to pivot away from the spraying arm, the centrifugal force being dependent on the weight of the deflector and the rotational speed of the arm. As the deflector pivots away from the arm, the angle of the stream relative to the rotation direction changes and the second "pushing" force decreases. The rotational speed of the arm will settle out when the first force and the third force reach an equilibrium point.

Figure 2:
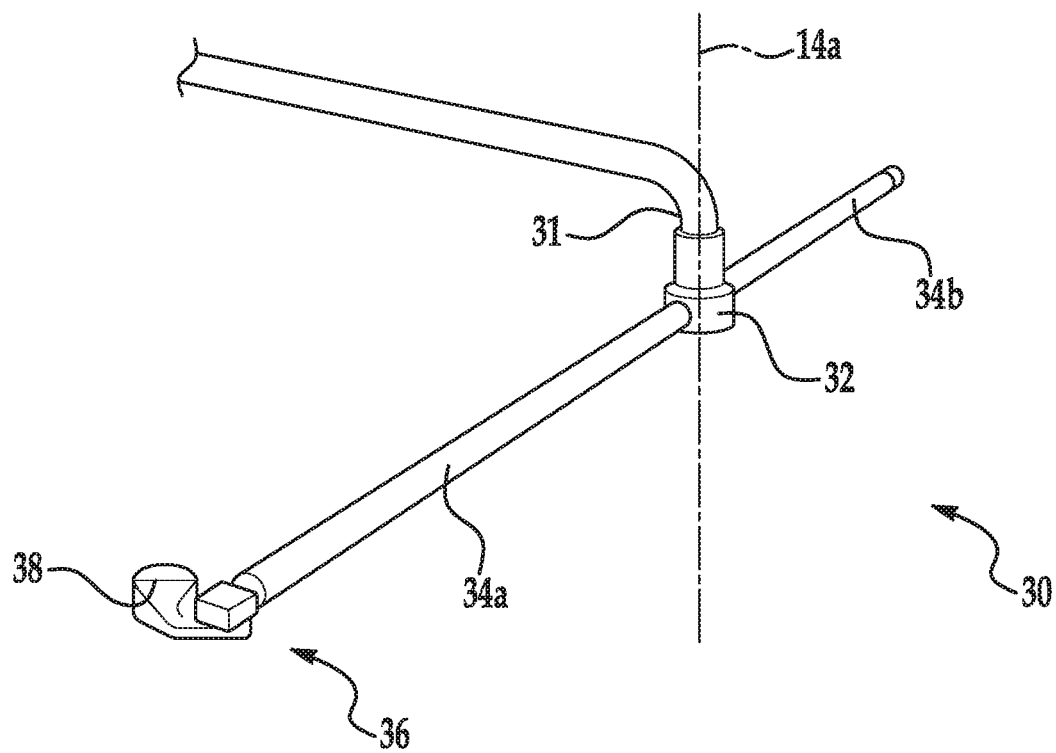
FIG. 2 is a perspective view of an exemplary spraying arm in accordance with the present invention.
Figure 3:
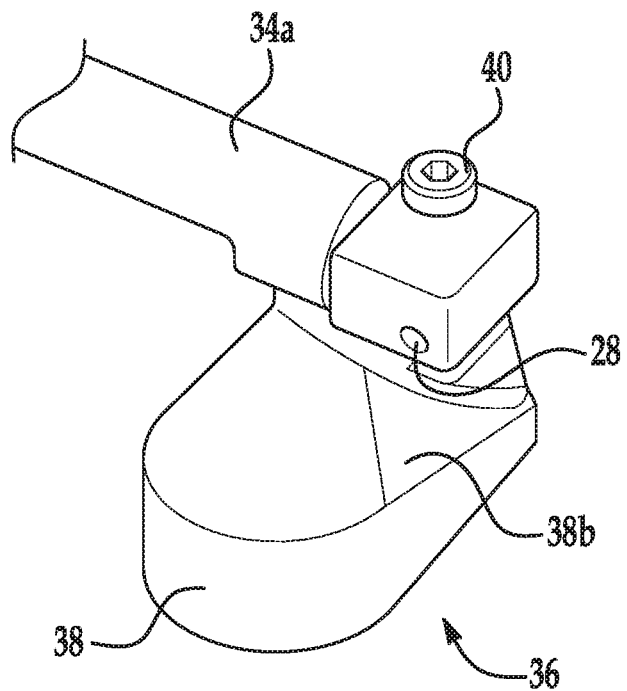
FIG. 3 is a perspective view of an exemplary deflector for regulating the speed of a spraying arm in accordance with the invention, where the deflector is pivoted away from the spray arm.
Figure 4:
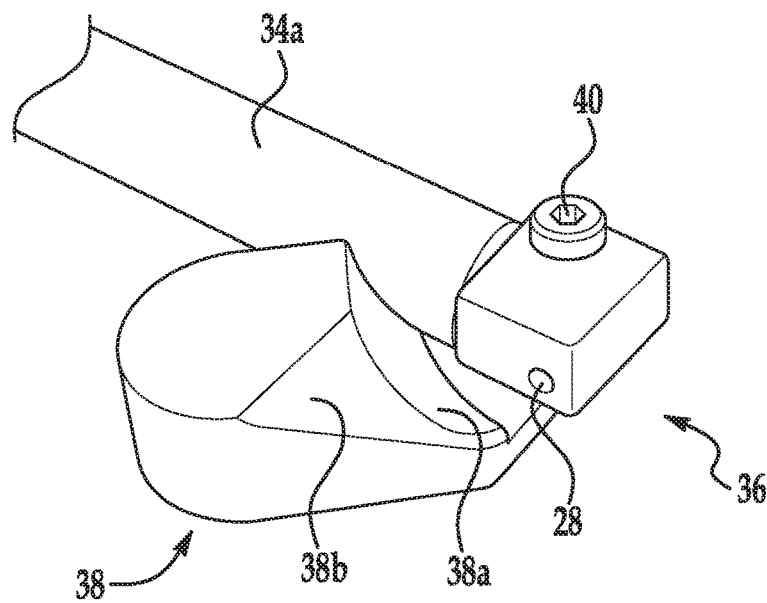
FIG. 4 is a perspective view of the exemplary deflector for regulating the speed of a spraying arm in accordance with the invention, where the deflector is pivoted toward the spray arm.

Referring now to FIG. 2, illustrated is an exemplary spraying arm 30 in accordance with the present invention in an "open" configuration (i.e., not within a spray compartment as in FIG. 1). The spraying arm 30, which is rotatable about an axis 14a, is attached to support 31 and includes a base 32 rotatable with respect to the support 31, a first arm portion 34a attached to the base 32, and a second arm portion 34b attached to the base, the second arm portion 34b diametrically opposite the first arm portion 34a. With additional reference to FIGS. 3-6, a first nozzle 28 is disposed on a distal end 36 of the first arm portion 32a, and a deflector 38 is pivotably connected at the first arm portion 32a at pivot point 40. In the illustrated embodiment the pivot point 40 is located radially inward relative to the nozzle 28, i.e., a distance from the pivot point 40 to the base is less than a distance from the nozzle 28 to the base 32. Thus, the deflector 38 is positioned adjacent the nozzle 28 to receive a stream of liquid emitted from the nozzle 28.

Figure 5:
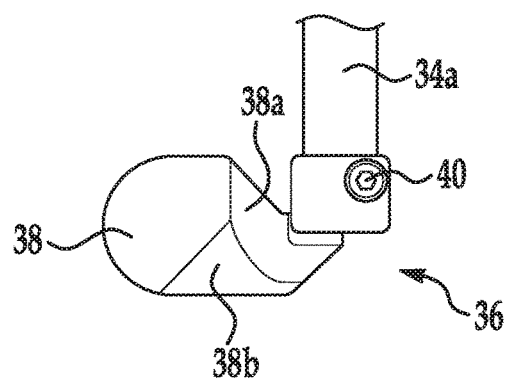
FIG. 5 is a top view of the exemplary deflector for regulating the speed of a spraying arm in accordance with the invention, where the deflector is pivoted away from the spray arm.
Figure 6:
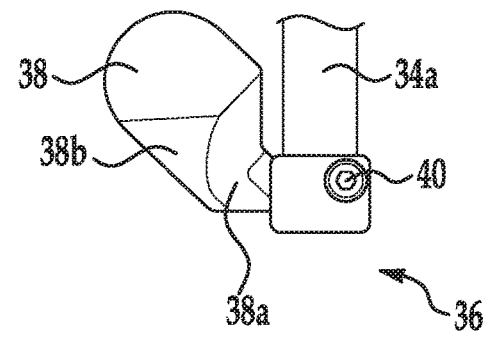
FIG. 6 is a top view of the exemplary deflector for regulating the speed of a spraying arm in accordance with the invention, where the deflector is pivoted toward the spray arm.

As noted herein, the deflector 38 includes curved surface 38a as best seen in FIGS. 5 and 6. Additionally, a surface of the deflector 38 distal from the nozzle 28 includes a chamfered portion 38b, where the chamfered portion causes a height of the curved surface 38a to be lowest at the front portion of the deflector 38 and increase in height moving toward the rear of the deflector. In the illustrated embodiment, the chamfered portion 38b stops approximately halfway toward the rear of the deflector 38. However, the chamfered portion may stop at different positions along the deflector 38 and also extend completely to the rear of the deflector 38.

The radius of the curved surface 38a and the chamfered portion 38b dictate the angle at which the liquid stream is dispersed relative to the rotation direction. In this regard, as the chamfered portion 38b is thickest the height of the curved portion is at its highest point (at the middle-rear of the deflector 38), causing the liquid stream to be deflected at a larger angle (e.g., producing fan spray pattern of approaching 90 degrees) relative to the rotation direction. As the thickness of the chamfered portion 38b decreases and the height of the curved portion decreases (toward the front of the deflector), the liquid stream is deflected at a smaller angle (e.g., producing a fan spray pattern approaching 10 degrees) relative to the rotation direction. Between the front and rear portions of the deflector 38 the fan spray pattern can be between 10 and 90 degrees depending on the specific region that the liquid stream strikes on the deflector 38.

Thus, maximum push force (and therefore maximum rotation speed) is achieved when the liquid stream strikes the front of the deflector 38 and minimum push force (and thus minimum rotation speed) is achieved when the liquid stream strikes the rear of the deflector 38. Between these two extremes the push force varies with the angle of the deflector 38 relative to the arm portion 32a.

In operation, the liquid emitted from the nozzle 28 strikes the deflector 38 and causes a force that tends to pivot the deflector 38 toward the first arm portion 32a. In this position, maximum push force is generated and the arm 32 begins to accelerate about the axis 14a. As the rotational speed increases, centrifugal force then works against the force created by the liquid stream and tends to pivot the deflector 38 away from the first arm portion 34a. The arm 32 will settle at a speed where these two forces reach equilibrium.

The actual rotational speed of the arm 32 is dictated by the pressure of the liquid stream emitted from the nozzle 28, the length of the arm portions 34a, 34b, the shape of the curved portion 38a and the chamfered portion 38b, the weight of the deflector 38, and the pivot point 40 of the deflector 38. Thus, any of these parameters may be adjusted to achieve a desired speed. However, in practice the arm length is dictated by the area to be cleaned and the pressure is typically set to a predetermined level that provides the best cleaning effect. Therefore, it may not make sense to vary these parameters to achieve a desired rotation speed of the arm 32. Instead, altering a shape of the curved portion 38a and chamfered portion 38b, altering the pivot point 40 of the deflector 38, and/or altering a weight of the deflector 38, are much more practical in reaching a desired rotation speed for the spraying arm 32.

In practice, a single deflector 38 arranged at one end of the arm 32 is sufficient to regulate a rotational speed of the spraying arm 32. However, it is possible to include a deflector on each end of the spraying arm. For example, a second nozzle can be disposed on the second arm portion, and a second deflector can be pivotably connected at the second arm portion to receive a stream of liquid emitted from the second nozzle.

Figure 7:
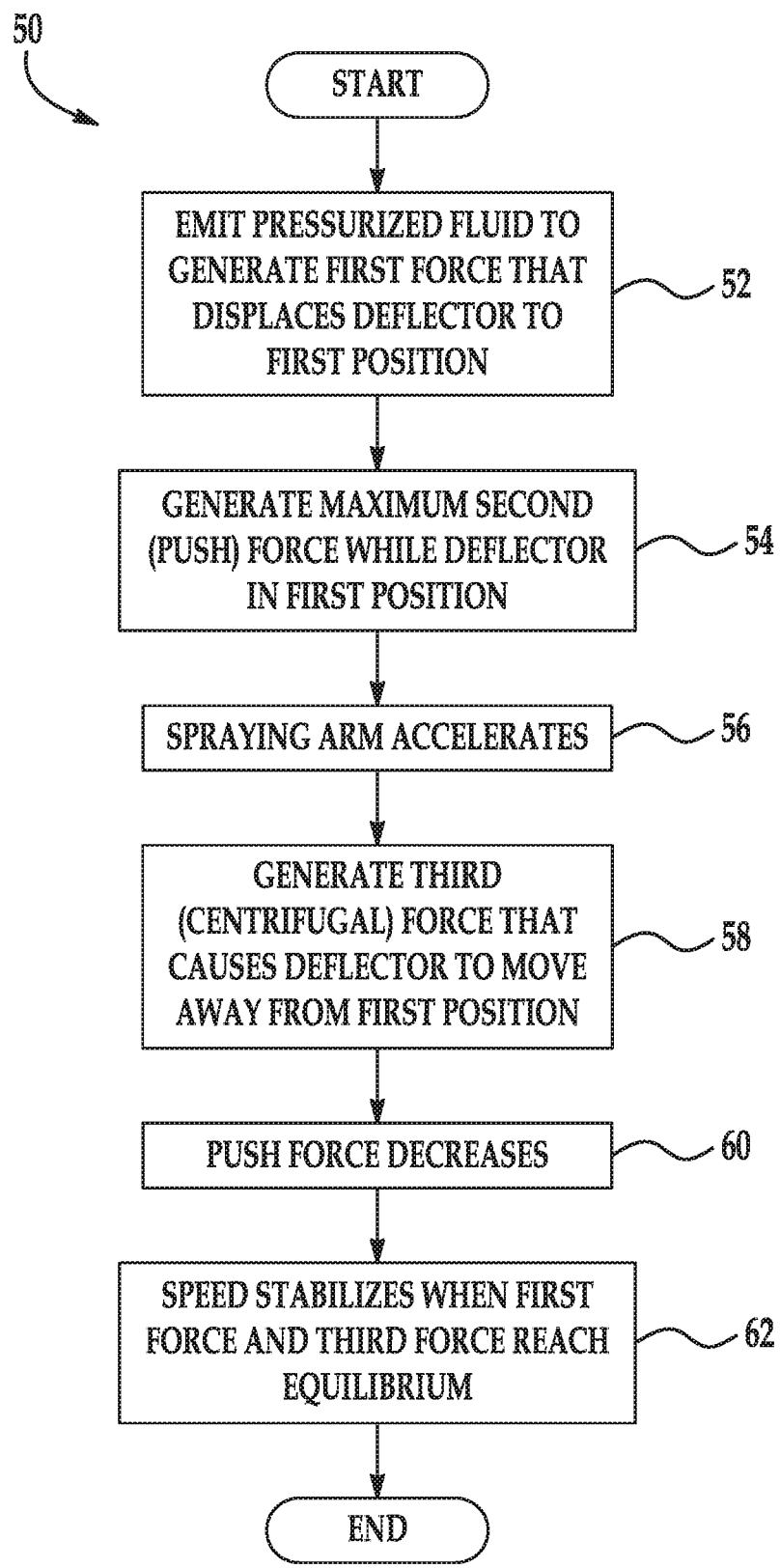
FIG. 7 is a flow chart illustrating exemplary steps for regulating the speed of a spraying arm in accordance with the present invention.

Referring now to FIG. 7, illustrated is a flow chart 50 depicting steps of an exemplary method for regulating the speed of a spraying arm 30 about an axis in accordance with the present invention. Variations to the illustrated method are possible and, therefore, the illustrated embodiment should not be considered the only manner of carrying out the techniques that are disclosed herein. Also, while FIG. 7 shows a specific order of executing functional logic blocks, the order of executing the blocks may be changed relative to the order shown. In addition, two or more blocks shown in succession may be executed concurrently or with partial concurrence. Certain blocks also may be omitted.

Beginning at block 52, pressurized liquid is emitted from the nozzle 28 located at a distal end 36 of the spraying arm 30. The pressurized liquid strikes the curved surface 38a of the deflector 38 with a first force, which tends to pivot the deflector 38 toward the arm 30. If the first force is sufficiently strong, the deflector 38 will pivot such that the deflector is immediately adjacent to the first arm portion 32a.

As the liquid is emitted from the nozzle 28 and deflected by the deflector 38, a second force is generated as indicated at block 54. This second force tends to push (rotate) the distal end 36 of the spraying arm 30 about the axis 14a. Assuming the liquid is emitted from the nozzle 28 at a fixed pressure, the magnitude of the second force then depends on the impact location on the curved surface 38. As noted above, the impact location can vary depending on the location of the deflector 38 about its pivot point 40. In this regard, the second "pushing force" is greatest when the deflector is pivoted toward the spraying arm and minimum when the deflector 38 is pivoted away from the spraying arm 30. This difference in the second force is due to the angle at which the emitted liquid is deflected off the curved surface 38a, the angle being minimum when the deflector 38 is pivoted toward the spraying arm 30 and maximum when the deflector 38 is pivoted away from the spraying arm 38.

When the spraying arm 30 is initially stationary, there is no force counteracting the first force and therefore the deflector 38 will pivot in toward the spraying arm 30 and therefore the second "pushing" force will be maximum. This second pushing force will cause angular acceleration of the spraying arm 30 about the axis 14a, as indicated at block 56.

As the spraying arm accelerates about the axis 14a, a third (centrifugal) force begins to act on the deflector 38 in a direction opposite the first force, as indicated at block 58. As the rotational speed increases, the third force also increases, causing the deflector to begin to move away from the spraying arm 30 and thus reducing the second "pushing" force, as indicated at block 60. The rotating speed of the spraying arm 30 will settle once the first force and the third force reach an equilibrium point (they are balanced), at which point a constant second (pushing) force is applied to the spraying arm 30 at a steady predefined speed as indicated at block 62.

Accordingly, the device and method in accordance with the invention can precisely regulate the rotational speed of a spraying arm, independent of a center pivot friction and manufacturing tolerances, such as spray nozzle orientation on the spray arm.

Although the invention has been shown and described with respect to a certain embodiment or embodiments, equivalent alterations and modifications may occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein exemplary embodiment or embodiments of the invention. In addition, while a particular feature of the invention may have been described above with respect to only one or more of several embodiments, such feature may be combined with one or more other features of the other embodiments, as may be desired and advantageous for any given or particular application.

Having described the invention, the following is claimed:

1. A device for a cleaning machine, comprising:
   an arm rotatable about an axis, the arm including a first arm portion and a second arm portion diametrically opposite the first arm portion;
   a first nozzle disposed on the first arm portion; and
   a first deflector pivotably connected to the first arm portion at a pivot axis of the first deflector and arranged to receive a stream of fluid emitted from the first nozzle;
   wherein fluid emitted from the first nozzle strikes the first deflector and causes a force that tends to pivot the first deflector toward the first arm portion to rotate the arm, and rotation of the arm about the axis causes a centrifugal force on the first deflector that tends to pivot the first deflector away from the first arm portion,
   wherein the first deflector has a first surface, a second surface arranged opposite the first surface in a first direction, the first direction parallel to the pivot axis of the first deflector, and a side surface that extends in the first direction between the first surface and the second surface, wherein each of the first surface and the second surface extend in a second direction that is perpendicular to the pivot axis of the first deflector, and
   wherein the first surface has a curved portion that faces the first nozzle and is arranged to receive the stream of fluid emitted from the first nozzle.

2. The device according to claim 1, further comprising a base, wherein the arm is rotatably connected to the base about the axis.

3. The device according to claim 1, wherein the pivot axis is located radially inward relative to an opening of the first nozzle that emits fluid.

4. The device according to claim 1, wherein the curved portion produces a fan spray pattern having a fan angle between 10 degrees and 90 degrees.

5. The device according to claim 1, wherein a pushing force of fluid deflected by the first deflector increases as the first deflector is pivoted toward the first arm portion.

6. The device according to claim 1, wherein a pushing force of fluid deflected by the first deflector decreases as the first deflector is pivoted away from the first arm portion.

7. The device according to claim 1, further comprising a chamfer disposed on the first surface and extending to the side surface.

8. The device according to claim 1, wherein fluid emitted by the first nozzle creates a force that rotates the arm about the axis; the force varying based on a distance of the first deflector relative to the first arm portion.

9. The device according to claim 1, wherein the first nozzle is arranged at an outer end of the first arm portion.

10. The device according to claim 1, further comprising:
    a second nozzle disposed on the second arm portion; and
    a second deflector pivotably connected at the second arm portion and arranged to receive a stream of fluid emitted from the second nozzle.

11. The device according to claim 1, wherein the arm has a longitudinal axis that intersects the axis of rotation, and the first nozzle emits fluid in a direction that is non-parallel to the longitudinal axis of the arm.

12. The device according to claim 1, wherein the arm has a longitudinal axis that intersects the axis of rotation, and the first nozzle emits fluid in a direction that is perpendicular to the longitudinal axis of the arm.

13. The device according to claim 1, wherein the first surface comprises a leading end distal from the arm, a trailing end proximal to the arm, and the curved portion is disposed between the leading end and the trailing end, wherein a height of the curved portion at the leading end is less than a height of the curved surface at the trailing end.

14. The device according to claim 1, wherein the first surface comprises a leading end distal from the arm and a trailing end proximal to the arm, the first surface having a chamfered portion at the leading end, wherein the curved portion is at the trailing end, the curved portion varying in height along the first surface, and in a region where the chamfered portion is thickest a height of the curved portion is a maximum.

15. The device according to claim 1, wherein the curved portion comprises a curved profile that varies in height along the first surface, and the nozzle is arranged to emit fluid onto the curved profile of the first surface.

16. The device according to claim 15, wherein as the first deflector pivots about the pivot axis fluid emitted by the nozzle strikes different portions of the curved profile.

17. The device according to claim 13, wherein the leading end and the trailing end move along a same arc about the pivot axis of the first deflector.

18. The device according to claim 13, wherein the curved portion moves about the pivot axis of the first deflector along a plane that is perpendicular to the pivot axis.

* * * * *